United States Patent [19]

Hendrickson et al.

[11] Patent Number: 4,514,569

[45] Date of Patent: Apr. 30, 1985

[54] SYNTHESIS OF 1-SUBSTITUTED ISOQUINOLINES

[76] Inventors: James B. Hendrickson, 9 Acacia St., Cambridge, Mass. 02138; César Rodriguez, 567 South St., Waltham, Mass. 02154

[21] Appl. No.: 343,407

[22] Filed: Jan. 28, 1982

[51] Int. Cl.$^3$ ............................................. C07D 217/20
[52] U.S. Cl. ...................................... 546/146; 546/14; 546/21; 546/44; 546/74; 546/139; 546/144
[58] Field of Search ........................... 546/146, 14, 144

[56] References Cited

U.S. PATENT DOCUMENTS 3,634,429  1/1972  Leimgruber et al. ................ 546/146
3,914,232  10/1975  Mohacsi et al. ...................... 546/146
4,139,534  2/1979  Lim et al. ............................. 546/146

OTHER PUBLICATIONS

Grewe, et al., "Chem. Ber.", vol. 100, 1967, pp. 1550–1558.
Beyerman, et al., "Rec. Trav. Chim. Pay-Bas", vol. 95, 1976, pp. 24–25, 184–188.
Rice, "J. Org. Chem.," vol. 45, 1980, pp. 592–601, 3135–3137.
Beyerman, et al., "Rec. Trav. Chim. Pay-Bas," vol. 97, 1978, pp. 127–130.
Olieman, et al., "Rec. Trav. Chim. Pay-Bas", vol. 79, 1978, pp. 31–35.
Akiba, et al., "Tetrahedron Letters", vol. 22, No. 49, 1981, pp. 4977–4980.

*Primary Examiner*—Glennon H. Hollrah
*Assistant Examiner*—James H. Turnipseed

[57] ABSTRACT

A method for the synthesis of particular isoquinoline compounds which are useful intermediates in the preparation of members of the family of opium alkaloids, such as morphine and codeine. Steps in the process include the acylation of the isoquinoline nitrogen; reaction of the acylated isoquinoline with a phosphorous compound; and condensation with a benzaldehyde derivative to yield a 1-benzyl isoquinoline.

16 Claims, No Drawings

SYNTHESIS OF 1-SUBSTITUTED ISOQUINOLINES

The present invention concerns a process for the preparation of certain isoquinoline compounds which can then be taken on to useful compounds such as morphine and codeine.

It is known that compounds of the following formula (VII) and product thereof by Birch reduction (VIII) are intermediates for the synthesis of morphine and codeine:

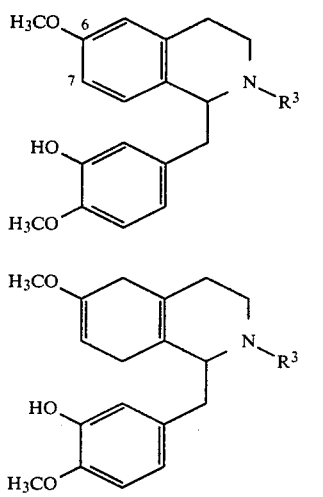

Wherein $R^3$ is —CHO, as seen in R. Grewe and W. Frederichsen, Chem. Ber. 100, 1550–1558 (1967). Other references disclose compounds similar to those of formulae (VII) and (VIII) with variations of substitution on the nitrogen of the isoquinoline ring, at the 6-position of the isoquinoline ring and at the para and both meta positions of the benzyl ring, all of which may be taken on to produce naturally occurring or synthetic alkaloids of the opium family.

SUMMARY OF THE INVENTION

The present invention comprises a process for the preparation of certain isoquinoline compounds which may be taken on to pharmaceutically useful natural and synthetic alkaloids of the morphine and codeine type as well as morphine and codeine themselves. Also part of the present invention are the intermediate products produced in the course of the process of the invention.

DETAILED DESCRIPTION OF THE INVENTION

The present invention may be appreciated by reference to the following Reaction Scheme 1:

Reaction Scheme 1

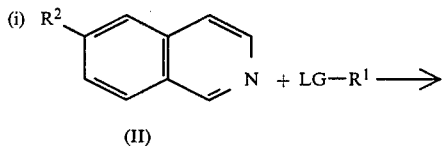

-continued
Reaction Scheme 1

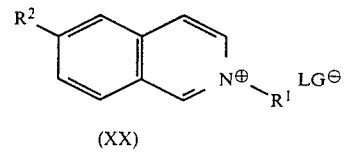

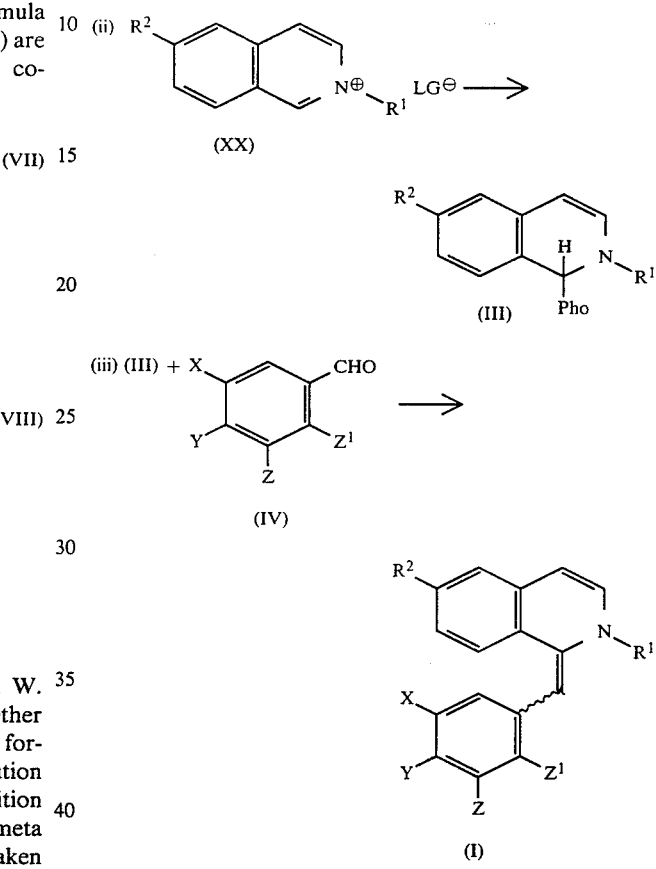

The compound of formula (I) has a double bond between the isoquinoline and benzyl groups whereby geometrical isomers are formed in step (iii). The wavy line between this double bond and the $XYZZ^1$ ring signifies that the compound of formula (I) comprises both isomers, i.e., that with $XYZZ^1$ ring cis or trans to the $R^2$ benzene ring of the isoquinoline group. Formula (I) may be reduced, e.g., by a Birch reduction to yield known intermediates, e.g. of the formulae (VII) and (VIII), for the synthesis of morphine and codeine as explained below.

In the above Reaction Scheme 1, $R^1$ is a substituted acyl group such as a moiety of the formula —COR wherein R is an organic moiety such as an alkyl, aryl or alkoxy group, examples of alkyl groups for R including lower alkyl groups, e.g. of about 1 to 6 carbons, examples of aryl groups including aryl of about 6 to 10 carbons, e.g. phenyl, and examples of alkoxy including lower alkoxy groups, e.g. of about 1 to 6 carbons, such as a methoxy, ethoxy, isopropoxy or tert-butoxy group; LG is a leaving group such as a halogeno, alkoxy or alkylthio group and in particular, LG may be a bromo, chloro, iodo, fluoro, lower alkoxy or lower alkylthio group, e.g. of about 1 to 6 carbons, such as an ethoxy group;

$R^2$ is hydrogen or an alkoxy, aryloxy or heterocyclicoxy group such as a substituted or unsubstituted alkoxy group, e.g. an unsubstituted lower alkoxy group such as an alkoxy group of about 1 to 6 carbons, it being apparent that many alkoxy, aryloxy or heterocyclicoxy groups and substitution thereof, may be used as the $R^2$ moiety in the process of the invention since the corresponding moiety in morphine and codeine is hydroxy and many substituents as $R^2$ may readily be reduced to hydroxy after preparation of the compound of formula (I) according to the invention;

Pho is a phosphorus containing moiety capable of being displaced from the compound of formula (III) by a Wittig reaction using n-butyl lithium and isovanillin, such as a phosphonate such as dialkylphosphonate, e.g. a di-loweralkyl phosphonate and in particular dimethylphosphonate, as explained below with respect to step (ii);

X and Z, which may be the same or different, are hydrogen, hydroxy, silyloxy, halogen, alkoxy, aryloxy, alkyl or aryl groups such as a hydrogen, hydroxy, trimethylsilyloxy, bromo, chloro, iodo or fluoro group or a substituted or unsubstituted lower alkoxy, phenoxy, lower alkyl or phenyl group and in particular X and Z may be hydrogen, hydroxy, bromo, methoxy, benzyloxy, or trialkyl- or triaryl-silyloxy groups such as triloweralkyl-silyloxy and triphenyl-silyloxy groups; Y is a hydroxy, silyloxy, halogen, alkoxy, aryloxy, alkyl or aryl group, such as a hydroxy, trimethylsilyloxy, bromo, chloro, iodo or fluoro group or a substituted or unsubstituted lower alkoxy, phenoxy, lower alkyl or phenyl group, and in particular, Y may be a trialkyl- or triaryl-silyloxy group such as triloweralkyl-silyloxy and triphenyl-silyloxy, or Y may be a lower alkoxy group such as methoxy; and $Z^1$ is hydrogen or halogen such as bromo, chloro, iodo or fluoro.

In the above definitions of X, Y and Z, the silyloxy group is used as a protected hydroxy. For example, in the formula (IV) starting material, if X is trimethylsilyloxy, the product of formula (I) initially has X as trimethylsilyloxy. However, the aqueous workup for compounds of formula (I), as set forth in Example 2, replaces the silyloxy group by hydroxy and it has been found that the use of the silyloxy protecting group much improves the yield of compounds of formula (I) compared with procedures utilizing the corresponding unprotected hydroxy.

In the above definitions and throughout this specification, lower alkyl and lower alkoxy may be of about 1 to 6 carbons.

Step (i) may be conducted at a temperature less than about 0° C. in a solvent, e.g. at about −10° C. in tetrahydrofuran under a neutral atmosphere such as under nitrogen. The particular ideal reaction conditions will depend on the particular reagent LG-$R^1$ used, e.g. for an alkyl halogenoformate such as ethyl chloroformate, the solvent can be tetrahydrofuran at about −10° C.

Step (ii) may be carried out by reacting the compound of formula (XX) from step (i) at a temperature less than about 20° C., in particular less than 0° C., in a solvent, e.g. at about −10° C. in an ether solvent such as tetrahydrofuran. The compound of formula (XX) cannot be isolated by known techniques and must be used in situ. The ideal reaction conditions to obtain the highest yields of the compound of formula (III) will depend on the particular phosphorus compound used, e.g. for a dialkylphosphonate such as dimethylphosphonate, the intermediate compound (XX) may be stirred at about 0° C. in tetrahydrofuran during slow addition of the phosphite or alkoxyphosphine such as trimethyl phosphite. If the intermediate compound of formula (III) is to be isolated, the reaction solution may be poured into a cold aqueous basic solution with a water-immisible solvent and extracted, e.g. it may be poured into aqueous potassium bicarbonate and methylene chloride, following by extraction, washing with a 5% hydrochloric acid aqueous solution, aqueous bicarbonated water and salt water brine and dried over sodium sulfate and evaporated. In step (ii) a phosphorus compound of the general formula $R^5R^5POCH_2R^6$ or $R^5R^5PSCH_2R^6$, wherein $R^5$ is aryl, alkyl or alkoxy such as lower alkyl or lower alkoxy and $R^6$ is aryl, hydrogen or alkyl such as lower alkyl, is reacted with the isoquinoline of formula (XX) whereby the phosphorus atom forms a bond with its unshared electron pair at the 1-position of the isoquinoline. The LG$\ominus$ anion then adds to the —$CH_2$— group of $R^5R^5PSCH_2R^6$ whereby $LGCH_2R^6$ is eliminated and a double bond forms from the phosphorus atom to the oxygen or sulphur atom. Values of $R^5$ and $R^6$ include methyl and phenyl.

Step (iii) may be conducted at a temperature less than about −60° C. in a solvent, e.g. at about −78° C. in an ether solvent such as tetrahydrofuran, preferably under a neutral atmosphere such as nitrogen. The 1-carbanion of compound (III) needed to react with the benzaldehyde of formula (IV) is produced by reacting compound (III) with a strong base such as an organometallic or nitrogen anion base, e.g. a lithium dialkylamide, an aryl lithium or an alkyl lithium such as methyl lithium, n-butyl lithium or phenyl lithium. Step (iii) may be done with or without isolation of the product of the previous steps.

The formation of the two isomers of the compound of formula (I), with respect to the cis or trans placement of the XYZ$Z^1$phenyl ring about the double bond, is not significant in the synthesis since the production of morphine and codeine may take place through the intermediates (VII) and (VIII) in which the double bond has been reduced. As used herein, "without isolation" indicates a reaction wherein at least one of the starting materials is in the reaction mixture resulting from its synthesis.

Compounds of formula (I) of the invention may be converted to compounds which are the precursors of morphine and codeine, which precursors are described, for example, by Beyerman et al. in Rec. Trav. Chim Pay-Bas (Journal of the Royal Netherlands Chemical Society), Vol. 95, p. 24 (1976); by Rice in J. Org. Chem., Vol. 45, p. 3135 (1980); by Rice et al. in J. Org. Chem., Vol. 45, p. 592 (1980); by Beyerman et al. in Rec. Trav. Chim. Pay-Bas, Vol. 97, p. 127 (1978); by Olieman, et al. in Rec. Trav. Chim. Pay-Bas, Vol. 97, p. 31 (1978); by Beyerman et al. in Rec. Trav. Chim. Pay-Bas, Vol. 95, p. 184 (1976); and by Grewe et al. in Chem. Ber., Vol. 100, p. 1550 (1967). For example, the compound of the invention of the following formula (V) may be produced according to the invention from the following compound (VI), also a part of the present invention:

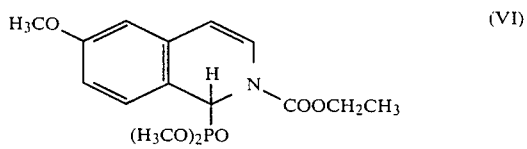
(VI)

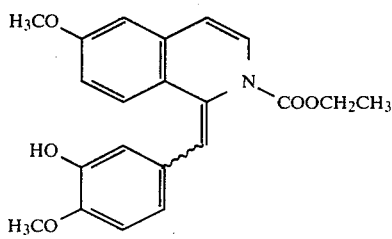

and the compound of formula (V) may be converted to the compounds of formulae (VII) and (VIII), which are known precursors of morphine and codeine by conducting Birch reductions on the compound of formula (V) to produce the tetrahydroisoquinoline of formula (IX) and the hexahydroisoquinoline of formula (X), respectively, wherein $R^2$ is $H_3CO$—; $R^4$ is —$OCH_2CH_3$; X is —OH; Y is —$OCH_3$; and Z and $Z^1$ are hydrogen, as exemplified below. The Birch-reduced products may then be hydrolyzed and decarboxylated with acid or base to produce the structure of formula (VII) and the structure of formula (VIII), respectively, wherein $R^3$ is hydrogen. Compounds of the formulae (VII) and (VIII) wherein $R^3$ is hydrogen may be converted to the compounds of formulae (VII) and (VIII) wherein $R^3$ is —CHO by refluxing with 1.5 equivalents of pure $C_6H_5OCHO$ in 10 volumes of ethyl acetate until homogeneous and then for about 0.75 hours until TLC shows the absence of starting material as set forth by K. C. Rice in J. Org. Chem., Vol. 45, No. 15, pages 3135 to 3137 (1980). Alternatively, the hydrolysis and decarboxylation to produce the corresponding NH compound, i.e. the corresponding compound which is unsubstituted at the 2-position of the isoquinoline ring, may take place before the Birch reduction e.g. on the compound of formula (V), or even after the Grewe cyclization, e.g. on a morphinan structure such as the compound of formula (XII). Further, the —$COOCH_2CH_3$ group of the compound of formula (V) may be left intact during the subsequent Birch reduction, Grewe cyclization and etherification forming the furan ring of morphine, whereby the —$COOCH_2CH_3$ group would be directly converted to a —$CH_3$ group, as is the substitution at the nitrogen in morphine and codeine, by reduction using a reducing agent such as lithium aluminum hydride in a 1:1 molar ratio at room temperature in an ether solvent such as diethyl ether or tetrahydrofuran. The reduction of the —$COOCH_2CH_3$ group to a —$CH_3$ group in the compound of formula (V) may also take place after the Grewe cyclization and before the etherification forming the furan ring of morphine.

Compounds of the invention of the formula (I) wherein $R^1$ is —COR and R is other than alkoxy are amides and may be reduced to amines, i.e. compounds of the structure of formula (I) wherein $R^1$ is hydrogen and $R^2$, X, Y, Z and $Z^1$ are as described above for compounds of formula (I), by treatment with lithium aluminum hydride. The thus-produced amine may then be N-formylated as described in J. Org. Chem., Vol. 45, No. 15, at page 3136 (1980). However formula (I) wherein $R^1$ is —COR and R is other than alkoxy, may be subjected to the Birch reduction as described herein and subjected to a Grewe cyclization and the —COR group is converted to the —$CH_3$ group on the nitrogen of morphine thereafter, e.g. by reduction to the unsubstituted amine and subsequent N-formylation and reduction to the N-methyl compound, see the methods described by H. C. Beyerman in the Rec. Trav. Chim. Pay-Bas articles mentioned above.

Also part of the present invention are compounds which are produced by the process of the invention and which are useful as intermediates in the synthesis of morphine and codeine. Compounds of the invention include those of formulae (I), (III), (V), (VI) and the following formulae (IX) and (X):

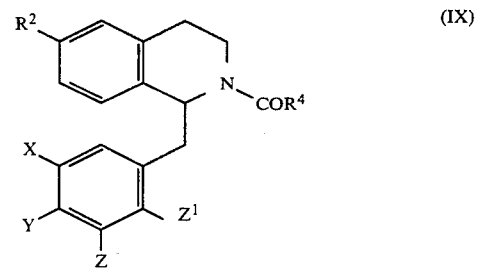

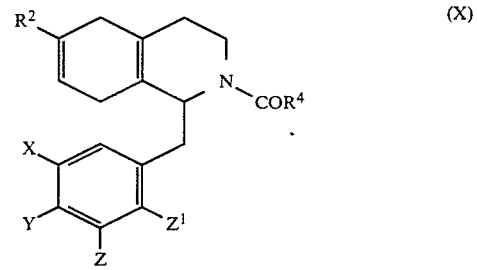

Wherein $R^2$, X, Y, Z and $Z^1$ are as described above for compounds of formula (I) and $R^4$ is alkyl, aryl or alkoxy as defined above for R, particularly lower alkoxy such as methoxy, ethoxy, isopropoxy or tert-butoxy. Thus, another aspect of the process of the present invention is the reduction e.g. a Birch reduction, of a compound of the formula (I) to yield one of the formula (IX) or (X), which may be referred to as step (iv). The reduction may be carried out in a liquid ammonia solvent using a dissolved alkali or alkaline earth metal, e.g. lithium, sodium, potassium or calcium but particularly lithium, as the reductant at a temperature of less than about the reflux temperature of −33° C., e.g. from about −80° to −33° C. and preferably about −33° C. for a period of time which will vary depending on the various substituents but generally about 15 minutes to avoid excessive reduction. It should be noted that if $Z^1$ is a halogen such as bromo, the Birch reduction will usually reduce this position to hydrogen. Conversion of compounds of formula (X) to literature precursors of morphine and codeine may be carried out by bromination and a Grewe cyclization, e.g. when $R^4$ is alkoxy, $R^2$ is hydrogen, X is hydroxy, Y is alkoxy such as methoxy and Z is hydrogen in formula (X), the compound may be brominated to yield a tribrominated product such as that of formula (XI) which may then be taken on to 1-bromo-N-carboalkoxy-norcodeine which has been converted in the literature to codeine, as in the following Reaction Scheme 2:

Reaction Scheme 2

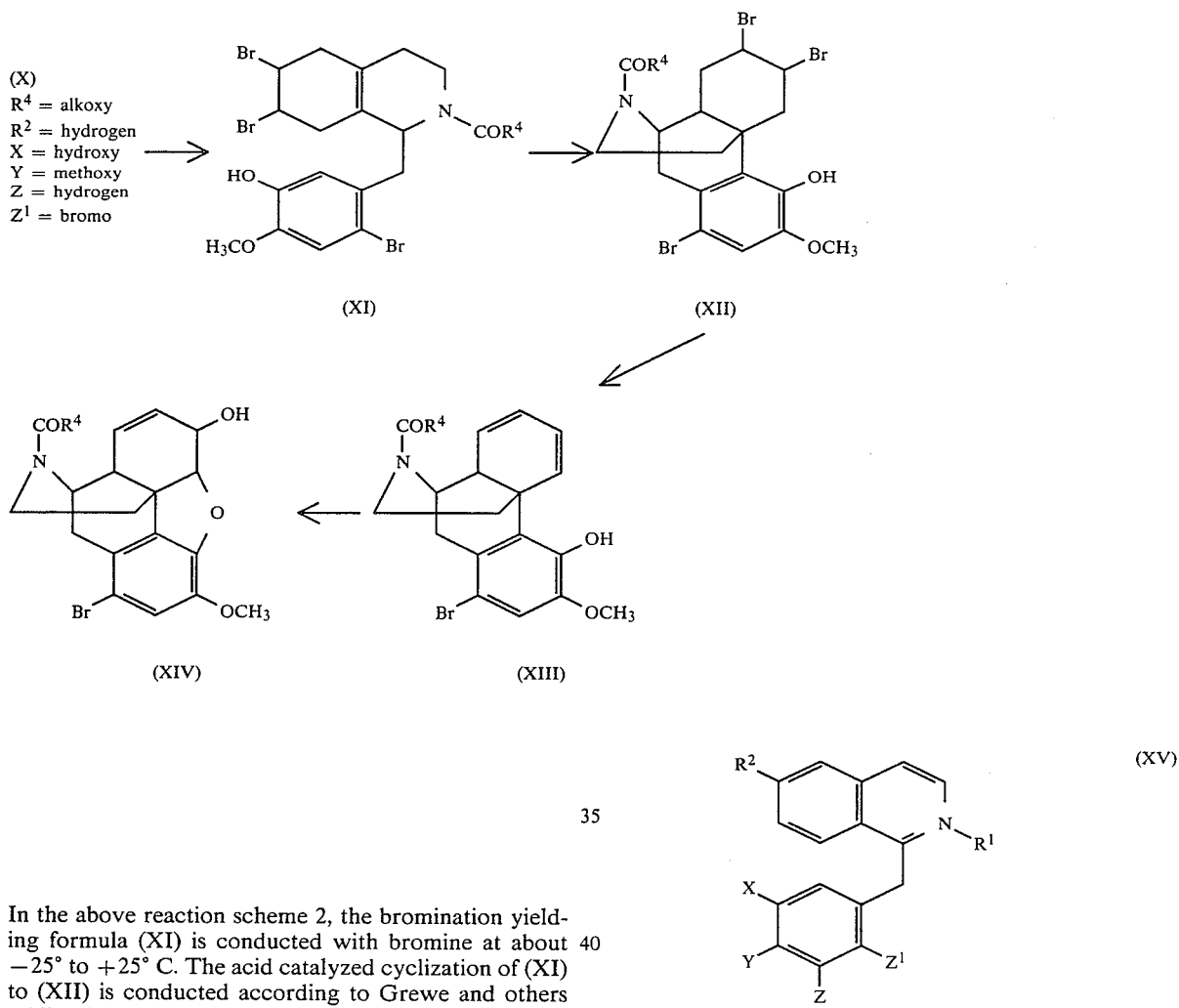

(X)
R⁴ = alkoxy
R² = hydrogen
X = hydroxy
Y = methoxy
Z = hydrogen
Z¹ = bromo

In the above reaction scheme 2, the bromination yielding formula (XI) is conducted with bromine at about −25° to +25° C. The acid catalyzed cyclization of (XI) to (XII) is conducted according to Grewe and others while the dehydrobromination of (XII) to produce (XIII) may be carried out with tertiary amine bases or hydroxides such as sodium or potassium hydroxide in a 2:1 molar ratio of base:(XII) at about −20° to +100° C. The reaction of formula (XIII) to give the ether compound (XIV) may be conducted with a peracid such as the peracid of an aryl or alkyl carboxylic acid, e.g. peracetic acid at about −25° to +25° C. The product of the peracid oxidation is (XIV) with the —OH up from the plane of the drawing and the ether —O—, which is vicinal to it, down. In contrast, the desired norcodeine has both the —OH and ether —O— vicinal to it cis to each other and down from the plane of the drawing of (XIV). However, the product of the peracid oxidation may be oxidized with MnO₂ or CrO₃ to yield the corresponding ketone at the hydroxy of formula (XIV) which is then reduced back to the hydroxy with sodium borohydride, the hydroxy then being cis to the ether —O— vicinal to it and down from the plane of the drawing of (XIV).

Another pathway to useful precursors of morphine and codeine and others of the opium-type alkaloids involves simple migration of the exo double bond of the compound of formula (I) into the isoquinoline ring system by warming with an acid such as hydrochloric acid to produce the compound of formula (XV):

wherein R¹, R², X, Y, Z and Z¹ are as described above for formula (I).

In the following examples and throughout this specification, the following abbreviations are used: gm (grams); ml (milliliters); °C. (degrees Centigrade); TLC (thin layer chromatography); C, H, N, O, Na, etc. (The universally accepted chemical symbols for the elements unless otherwise indicated); and NMR (nuclear magnetic resonance).

EXAMPLE 1

Dihydroisoquinoline Phosphonate (III)

To a solution of 14 gm (0.11 mole) of isoquinoline in 40 ml of tetrahydrofuran is added 10 gm (0.09 mole) of ethyl chloroformate slowly at −10° C. with stirring under nitrogen and the mixture is stirred to a uniform suspension at −10° C. after which it is warmed to 0° C. and 11.6 gm (0.09 mole) of trimethyl phosphite is slowly added. The mixture is allowed to come to room temperature and stirred for 30 minutes. If the intermediate (III), wherein R² is hydrogen, R¹ is —COOCH₂CH₃ and Pho is (H₃CO)₂PO, is to be isolated, the solution is poured into an aqueous potassium bicarbonate-methylene chloride mixture, after which it is extracted, washed with a 5% by volume hydrochloric acid solution, a sodium bicarbonate aqueous solution and a sodium chloride aqueous solution, after which it is dried over sodium sulfate and evaporated to 23.7 gm of an oil (82% yield), the purity being established by TLC and NMR as follows (δ units): 1.3 (3H, triplet); 3.5 (3H, doublet); 3.6 (3H, doublet); 4.2 (2H, multiplet); and 7.0 (5H, multiplet).

EXAMPLE 2

Wittig Adduct (I)

A solution of n-butyl lithium (0.09 mole) is added to the tetrahydrofuran solution of compound (III) cooled to −78° C. and prior to the isolation procedure described in Example 1. The solution turns a deep red and is allowed to stir for 15 minutes at −78° C. To the solution is added neat or in a tetrahydrofuran solution, 3, 4-dimethoxybenzaldehyde, compound (IV) wherein X and Y are $H_3CO—$, and Z and $Z^1$ are hydrogen, in an amount of 0.085 moles. The solution is allowed to warm with stirring to room temperature and stirred for three hours or until the aldehyde has disappeared by TLC. The mixture is quenched by pouring into cold aqueous brine and extracted with methylene chloride. The organic layer extract is washed with a sodium chloride aqueous solution, dried over magnesium sulfate and evaporated to an oil which can be purified by passage through silica gel with a 15% by volume ethyl acetate in hexane solvent to yield (I), wherein $R^1$ is $—COOCH_2CH_3$; $R^2$ is H; X and Y are $H_3CO$ and Z and $Z^1$ are H, presumably as a mixture of cis and trans isomers characterized by an NMR with an olefinic singlet at about 6.4–6.5δ and an aromatic envelope including the isoquinoline olefinic protons centered at 7.0δ.

In a manner similar to the above procedure, the following aldehydes of formula (IV) may be reacted with the phosphonate (III) of Example 1: isovanillin (3-hydroxy-4-methoxybenzaldehyde), 6-bromo-isovannillin and 0-trimethylsilyl-isovanillin.

EXAMPLE 3

1-Benzyl-isoquinoline (XV)

The Wittig product (I), wherein $R^1$ is $—COOCH_2CH_3$, $R^2$ is hydrogen, X and Y are $H_3CO—$ and Z and $Z^1$ are hydrogen, from Example 2 is added to a 10% by volume concentrated HCl in methanol solution and warmed to about 60° C. for about 30 minutes, poured onto ice and washed with chloroform. To the aqueous phase is added an aqueous ammonium hydroxide solution which is then extracted with methylene chloride, dried over sodium sulfate and evaporated to yield the isoquinoline of formula (XV), wherein $R^1$ is $—COOCH_2CH_3$, $R^2$ is hydrogen, X and Y are $H_3CO—$ and Z and $Z^1$ are hydrogen.

In a manner similar to the above procedure, the following isoquinolines of formula XV are prepared wherein $R^1$ is $—COOCH_2CH_3$, $R^2$ is hydrogen, Y is $H_3CO—$ and Z is hydrogen: X is hydroxy and $Z^1$ is hydrogen; and X is hydroxy and $Z^1$ is bromo.

EXAMPLE 4

Hexahydroisoquinoline (X)

To 1.1 gm of the Wittig product (I), wherein $R^1$ is $—COOCH_2CH_3$, $R^2$ is hydrogen, X and Y are $H_3CO—$ and Z and $Z^1$ are hydrogen, from Example 2 is added 35 ml of tetrahydrofuran and 18 molar equivalents of tert-butanol and 140 ml of liquid ammonia solution at −78° C. To the solution is then added 15 molar equivalents of lithium metal. The solution is then refluxed at −33° C. for no more than 15 minutes after which it is quenched by cooling to −78° C. and the addition of about 20 molar equivalents of solid ammonium chloride. On warming, the ammonia evaporates and thus controls the temperature at about −33° C. until it is mostly gone. The reaction mixture is then quenched by adding an equal volume of a saturated aqueous ammonium chloride solution. The aqueous phase is then extracted with chloroform, dried with sodium sulfate and passed through a silica gel column using a 6:1 ethyl acetate: hexane mixture. The product is evaporated to yield (X), wherein $R^4$ is $—OCH_2CH_3$; $R^2$, Z and $Z^1$ are hydrogen and X and Y are $H_3CO—$. The NMR of the product shows a characteristic aromatic envelope centered at 6.7 to 7.0δ and a two proton singlet at 5.6δ.

In a manner similar to the above, the following two compounds of formula (X) are also prepared: $R^2$ is hydrogen, $R^4$ is $—OCH_2CH_3$, X is $—OH$, Z and $Z^1$ are hydrogen and Y is $—OCH_3$; and $R^2$ is $—OCH_3$, $R^4$ is $—OCH_2CH_3$, X is $—OH$, Z and $Z^1$ are hydrogen and Y is $—OCH_3$, this latter compound being also defined as being of the formula (VIII) wherein $R^3$ is $—COOCH_2CH_3$.

EXAMPLE 5

Tetrahydroisoquinoline (IX)

If the procedure of Example 4 is modified by limiting the lithium to 8 molar equivalents and substituting 8 molar equivalents of dry solid ammonium chloride in place of the tert-butanol in the reduction medium, the procedure affords the tetrahydroisoquinoline of formula (IX) wherein $R^4$ is $—OCH_2CH_3$, $R^2$ is hydrogen, X and Y are $H_3CO—$ and Z and $Z^1$ are hydrogen. The NMR of the product has a full four-proton aromatic singlet at 7.0δ for the isoquinoline aromatic ring.

In a manner similar to the above, the following two compounds of formula (IX) are also prepared: $R^2$ is hydrogen, $R^4$ is $OCH_2CH_3$, X is $—OH$ and Y is $—OCH_3$; and $R^2$ is $—OCH_3$, $R^4$ is $—OCH_2CH_3$, X is $—OH$ and Y is $—OCH_3$, this latter compound being also defined as being of the formula (VIII) wherein $R^3$ is $—COOCH_2CH_3$.

EXAMPLE 6

Direct Production of Hexahydoisoquinoline (X)

The procedures of Examples 1 and 2 are followed without isolation of the intermediate phosphonate of formula (III). The reaction solution resulting from the Wittig reaction of Example 2 is cooled to −78° C. and the procedure of Example 4 is followed with the addition of ammonia followed by 15 molar equivalents each of tert-butanol and lithium metal. The solution is refluxed at −33° C. for no more than 15 minutes and is then worked up as in Example 4 to yield the hexahydroisoquinoline derivative of formula (X) wherein $R^4$ is $—OCH_2CH_3$; $R^2$, Z and $Z^1$ are hydrogen; and X and Y are $H_3CO—$.

EXAMPLE 7

Hexahydroisoquinoline (X)

The procedures of Example 6 are followed utilizing 6-methoxyisoquinoline of the formula (II), wherein $R^2$ is $H_3CO—$, as the starting material to yield the compound of formula (X) wherein $R^4$ is $—OCH_2CH_3$, $R^2$ is $H_3CO—$, X is OH, Y is $—OCH_3$, and Z and $Z^1$ are hydrogen. This compound may also be described as being of the formula (VIII) wherein $R^3$ is $—COOCH_2CH_3$.

What is claimed is:

1. A method of preparing a morphine intermediate of the following formula (I):

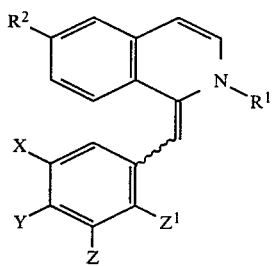

wherein
$R^1$ is COR group wherein R is $C_{1-6}$ alkyl, phenyl, or $C_{1-6}$ alkoxy;
$R^2$ is hydrogen or $C_{1-6}$ alkoxy;
X and Z, which may be the same or different, are hydrogen, hydroxy, silyloxy, halogen, lower alkoxy, phenoxy, lower alkyl, trimethylsiloxy, phenyl, or benzyloxy;
Y is hydroxy, silyloxy, halogen, lower alkoxy, phenoxy, phenyl, or lower alkyl;
$Z^1$ hydrogen or halogen, comprising the following steps
(i) reacting an isoquinoline of the following formula (II):

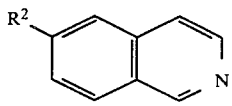

wherein $R^2$ is as defined above, with a compound of the formula LG-$R^1$, wherein LG is mercapto, hydroxy, halogeno, lower alkoxy, or lower alkylthio and $R^1$ is as defined above, followed by
(ii) reacting the N-acylated produce of step (i) with a phosphorus compound capable of being displaced from the compound of the following formula (III) as the Pho moiety by a Wittig reaction using n-butyl lithium and isovanillin, to yield a compound of the following formula (III):

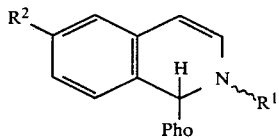

wherein Pho is a phosphonate PO(OR)$_2$ wherein R is lower alkyl. $R^1$ and $R^2$, are as defined above; and
(iii) reacting the compound of formula (III) in a Wittig reaction with the benzaldehyde of the following formula (IV):

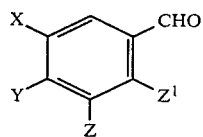

wherein X, Y, Z, and $Z^1$ are as defined above, to yield a compound of formula (I).

2. The method of claim 1, wherein at least one of X and Z is not hydrogen.

3. The method of claim 1, wherein
R is alkoxy;
$R^2$ is lower alkoxy;
X and Z, which may be the same or different, are hydrogen, hydroxy, bromo or benzyloxy, with the proviso that at least one of X and Z are not hydrogen;
Y is lower alkoxy;
$Z^1$ is bromo;
LG is halogeno.

4. The method of claim 1, wherein steps (i) and (ii) are conducted without isolation of the product of step (i).

5. The method of claim 1, wherein steps (i), (ii) and (iii) are conducted without isolation of the products of steps (i) and (ii).

6. The method of claim 1, wherein step
(i) is conducted in a solvent at a temperature less than about 0° C.;
(ii) is conducted in a solvent at a temperature less than about 20° C.; and
(iii) is conducted by the addition of an alkyl lithium at a temperature less than about −60° C. after which the benzaldehyde of formula (IV) is added.

7. The method of claim 1, wherein LG is a chloro group.

8. The method of claim 1, wherein $R^2$ is hydrogen.

9. The method of claim 8, wherein
X and Y are methoxy; and
Z and $Z^1$ are hydrogen.

10. The method of claim 1, wherein
$R^1$ is —COR$^4$ and $R^4$ is alkoxy;
$R^2$ is hydrogen;
X is hydroxy;
Y is alkoxy; and
Z is hydrogen.

11. The method of claim 1, wherein $R^1$ is a moiety of the formula —COR and R is an alkoxy group.

12. The method of claim 1, wherein in step (i), LG-$R^1$ is an alkyl halogenoformate.

13. The method of claim 12, wherein said alkyl halogenoformate is ethyl chloroformate.

14. The method of claim 1, wherein step (ii), said phosphorus compound is of the formula $R^5R^5POCH_2R^6$ or $R^5R^5PSCH_2R^6$ wherein $R^5$ is aryl, alkyl or alkoxy and $R^6$ is aryl, hydrogen or alkyl.

15. The method of claim 14, wherein said phosphorus compound is trimethyl phosphite.

16. The method of claim 1, wherein step (iii) is conducted in the presence of a strong base.

* * * * *